United States Patent [19]

Thirumalachar et al.

[11] 4,082,613

[45] Apr. 4, 1978

[54] PROCESS FOR THE PRODUCTION OF INSULIN BY GENETICALLY TRANSFORMED FUNGAL CELLS

[75] Inventors: Mandayam J. Thirumalachar; Mandayam J. Narasimhan, both of Bangalore, India; John A. Anderson, St. Paul, Minn.

[73] Assignee: The Regents of the University of Minnesota, Minneapolis, Minn.

[21] Appl. No.: 679,565

[22] Filed: Apr. 23, 1976

[51] Int. Cl.$^2$ ............................................. C12D 13/02
[52] U.S. Cl. .......................................... 195/76; 195/1; 195/80 R; 195/1.8; 195/81
[58] Field of Search ...................... 195/28 N, 76, 81, 1

[56] References Cited

PUBLICATIONS

Vanek et al., Genetics of Industrial Microorganisms, vol. II, p. 38, Elsevier Pub. Co., 1973.
Willmer, Cells and Tissues in Culture, vol. 2, p. 674, Academic Press, 1965.

*Primary Examiner*—Alvin E. Tanenholtz
*Attorney, Agent, or Firm*—Burd, Braddock & Bartz

[57] ABSTRACT

A process for the production of insulin using fungal cells. Human insulin producing cells are extracted to obtain the functional genome (the genetic material which determines the capacity of the cells to produce insulin) which is used to transform fungal cells, making them capable of producing insulin. The insulin has been extracted and identified by radioimmune assay and by bioassay. The same process can also be applied to produce animal insulins using specific specie transforming functional insulinogenic genomes. A process for serial secondary culture of insulin producing cells is disclosed. The significance of the invention is related to the great need to produce human insulin in large amounts. Human insulin has distinct biological and clinical advantages when compared with commercially available animal insulins now used for the treatment of diabetes mellitus in man.

6 Claims, No Drawings

PROCESS FOR THE PRODUCTION OF INSULIN BY GENETICALLY TRANSFORMED FUNGAL CELLS

BACKGROUND OF THE INVENTION

This invention relates broadly to the field of medical biology and more specifically to:
 (a) Endocrinology, physiology and clinical medicine
 (b) Microbiology and cell transformation
 (c) Human cell and microbial cell fermentation systems.

Since the time of the discovery of the hormone insulin and its use in the treatment of humans with diabetes mellitus, insulin has been obtained and prepared commercially from bovine and porcine pancreas. Human insulin from human pancreas has been achieved only on a laboratory scale. Insulins from a host of animal species ranging from fish to elephants and whales have been isolated and studied on a laboratory scale. In recent years, the shortage of bovine and porcine pancreas has necessitated a search for insulin production from other sources or by other processes. Moreover, although bovine and porcine insulins have been used for several years, disadvantages exist due to the species and immunologic differences which are known to incite anti-insulin antibody formation in man following prolonged use. Hence, methods for achieving production of human insulin, which is highly advantageous both in terms of bioactivity and non-antigenicity, have been under study by several scientists.

Two approaches have been tried to produce human insulin. These are: (1) chemical synthesis of human insulin, and (2) the production of human insulin by cultivation of human insulin producing beta cells by in vitro tissue culture systems. Chemical synthesis of human insulin on a large scale has not as yet been achieved due to the complexity of the chemical steps involved in the synthesis as well as the multifold cost of such synthesis procedures as compared with the present cost of producing bovine-porcine insulin. In regard to tissue culture, all methods reported thus far involve primary cultures of small explants or primary monolayers of insulin producing pancreatic beta cells obtained from a host of animal species as well as man. However, such primary cultures do not survive long and cannot be propagated serially to achieve a sufficient number of beta cells in order to produce insulin on a large scale.

The present inventors have also discovered a new technique of growing both animal and human beta epithelioid cells producing insulin in serial secondary cultures, as described, by which one can achieve reasonable amounts of human or animal insulin. This new technique, although far superior to other tissue culture methods described by others, is at present not sufficient to obtain insulin or human insulin on a large scale since the rate of proliferation of human beta cells in vitro culture is relatively limited. Hence, the present invention includes a new process wherein one transforms a rapidly proliferating cell system with genetic information obtained from human insulin producing cells to produce human insulin on a large scale.

In the field of microbiology, several experiments have been performed over the past few years to transform cells. These include:
 (1) Transformation of rate of growth, morphology and structure
 (2) Transformation of function
 (3) Inter-combination of (1) and (2).

(1) Transformation of rate of growth and morphology and structure has been achieved using physical agents such as X-rays, alpha, beta and gamma ray irradiations; by chemical methods using chemical mitogens both organic and inorganic and microbial metabolites such as those belonging to the Actinomycin group; and by biological means by placing cells in foreign environments or growing them in contact with other types of cells to achieve an inter-cell communication response. Examples of these range from the transformation of specialized ectodermal cells to keratinized and even fibroblastic cells when placed in exposed or hostile environments, to the transformation of bacteria to resistant strains when placed in prolonged or chronic contact with small sublethal doses of the respective antibiotics.

(2) Transformation of function or part of the functions or functional characteristics has been achieved with the bacteria *E. coli*. *E. coli* that were susceptible to one antibiotic were transformed into a resistant strain by transfer of the genetic material (DNA) from another *E. coli* strain that was already resistant to the particular antibiotic. This has been achieved by extracting plasmid, DNA, from the resistant bacteria and transferring it to a non-resistant strain by using a virus as a carrier. This has been extended by serial transfers to obtain a *E. coli* strain resistant to several antibiotics by transforming a susceptible non-resistant strain with genetic material (DNA) from different *E. coli* resistant to different antibiotics.

Finally, *E. coli* has been transformed to produce a single protein sequence contained in the toad bladder by transferring genetic material (DNA) from cells from the toad bladder.

In all these above cited instances, purified or native DNA has been used as the gene-information carrying the transforming principle and a virus has been employed to carry the genetic information from the parent transforming cell to the recipient transformed cell. Hence, it is possible that besides the appearance of the functional characteristics of the donor *E. coli* or toad bladder cell in the recipient transformed cell, there may also appear the functional characteristics in terms of protein sequences of the carrier virus which also becomes incorporated into the genetic sequence of the transformed cell.

Biotransformation in antibiotic producing cultures has been successfully achieved by one of the inventors. *Streptomyces aurofaciens* which produces chlortetracycline was biotransformed, using the functional genome from *Streptomyces pimprina* which produces the antifungal antibiotic thiolutin. The biotransformed *Streptomyces aureofaciens* in addition to producing chlortetracycline, also produced thiolutin.

The inventors have also transformed functionally non-specific human squamous cells from the buccal (oral) cavity with the functional genome from human insulin producing cells to make the buccal cells produce insulin, as measured by specific radioimmune assay.

For transforming a rapidly proliferating cell system such as microorganisms with the genetic materials from human insulin producing cells, the bacterium *E. coli* has been studied by several workers. However, this has not been successful so far. *E. coli* which is a prokaryotic cell (without a definitive nucleus) would appear to be a poor model to attempt transformation with genetic materials from evolved eukaryotic cells (with a definite nucleus), since the *E. coli* would not have the appropriate nuclear network to incorporate genetic segments from human cells concerned with insulin production. Also, *E. coli* is not known to produce any long chain amino acids which would be essential to synthesize insulin. However, fungi which proliferate rapidly are eukaryotic cells and are known to produce long chain amino acid sequences as some antibiotics. Hence, we have used a primitive fungus for transformation with the functional genome from human insulin producing cells to produce insulin.

DESCRIPTION OF PRIOR ART

Bacterial cells (*E. coli*) have been transformed with genetic materials from other *E. coli* and human and animal cells have been transformed with genetic materials from other virally infected (oncogenic and other viruses) human and animal cells respectively. However, there is no known description of the transformation of primitive microorganisms, such as a fungus, with genetic materials, from human cells with a capacity to produce a very specialized or specific substance to enable the microorganism to produce the specific substance, namely, the production of insulin by these primitive microorganisms.

SUMMARY OF THE INVENTION

Broadly stated, the invention comprises a process for the production of insulin by genetically transformed fungal cells. More specifically, the invention comprises a process for producing insulin in which pancreatic cells, either human or other animal species, are dispersed in a selective-differential nutrient amino acid-rich medium composition and incubated under open aeration cell growth conditions to grow insulin producing beta cells. The resulting culture is serially sub-cultured several times until the optimum desired amount of cells is achieved. The functional genomic material which determines the capacity of the cells to produce insulin is extracted from the cells. The latter is dispersed in a further nutrient amino acid-rich medium in an incubation vessel. This dispersion is then inoculated with a new species of fungus of the genus Trichosporon isolated from the soil and designated as TC-1176. A deposit of the new soil Pseudosaccharomycete TC-1176 has been made in accordance with the notice of Apr. 29, 1971 (866 O.G. 638) in the American Type Culture Collection, Rockville, Md., and is identified as ATCC 20,477.

This culture is incubated under cell growth conditions in the presence of an anti-fungal membrane permeability agent and mitogen to incorporate the functional genome into the fungal cell structure. The resultant bio-transformed fungal cells are transferred to a carbohydrate-nitrogen-rich medium which is maintained under cell growth conditions until the desired optimum fungal growth level has been reached. Thereafter the cells are separated from the media and the insulin is extracted from the cells and supernatant media using conventional techniques.

DETAILED DESCRIPTION OF THE INVENTION

The detailed procedures employed in the extraction of the functional genome; the methods of transformation of the fungal cells and the cultivation and other characteristics of the transformed fungal cells are as follows:

I. Cultivation of the Selective Free Cell System of Beta Epithelioid Cells

The pancreas is obtained by sterile dissection techniques, preferably from human fetuses at autopsy, and is separated from the covering peritoneal membrane, minced into fine pieces using a curved iris scissors and the flat edge of a BD 19 scalpel blade, following which the minced fragments are trypsinized in 0.125% trypsin at about 32° to 39° C (optimum 37° C) for 30 minutes; the cells centrifuged and the residual trypsin neutralized by suspending the cells in the culture media. The cells are cultured as free suspended cells for 4 days at about 32° to 39° C (optimum 37° C) in sterile plastic flasks with open air vent caps with 8 to 16 liters of air per minute, circulating in the incubator provided with water troughs for moisture. The media (medium alpha HC) is a selective differential medium which permits selective proliferation of insulin producing beta epithelioid cells.

An exemplary nutrient medium rich in amino acids is that known as Medium 199 with Earle's base (Proc. Soc. Exp. Biol. Med., 73:1, 1950, Growth, 15:11, 1951, Proc. Soc. Exp. Biol. Med., 74:22, 1950; Proc. Soc. Exp. Biol. Med., 78:880, 1951; J. Cell & Comp. Physiol., 36:411, 1950; J. Am. Med. Assn., 151:1081, 1953). To each liter of medium there is added from about 5 to 20 ml of liver extract, preferably about 10 ml; about 5 to 20 mg of hydrocortisone sulphate, preferably about 12.5 mg; and minor amounts of anti-biotic and anti-fungal agents.

A preferred nutrient composition for culturing the pancreatic cells in our Medium alpha HC, the composition of which is as follows:

| | |
|---|---|
| Medium 199 with Earle's base GIBCO (Grand Island Biological Company) | 100 ml |
| Liver extract (injectable) (Lexavite-Lilly) | 1.0 ml |
| Hydrocortisone Sulphate | 1.25 mgs |
| Crystalline penicillin | 50,000 units |
| Streptomycin Sulphate | 50 mg |
| Nystatin, a polyene anti-fungal anti-biotic | 5,000 units |

Following 4 days of culture in the above differential culture medium, the cultures are sub-cultured with Medium alpha which has the same constituents as Medium alpha-HC, but without hydrocortisone sulphate. Every 4 to 8 days the flasks are sub-cultured by dividing the volume of medium and cells into two aliquots and reconstituting with the addition of an equal volume of fresh medium. Insulin assays using radioimmune techniques are done every 8th day prior to the next sub-culture.

II. The Extraction of the Macromolecular Functional Genome

The functional genome may be extracted by any of several alternative methods, as follows:

(A) The cultures (cells + medium) produced by Method I contained immune reacting insulin (IRI), in the range of 80 to 100 microunits/ml. Following such 3 and 6 serial sub-cultures, 10 ml of the culture media containing cells after sub-culture for 8 days was centrifuged at 1800 to 2000 rpm for 20 minutes, the supernatant recentrifuged at 2800 to 3000 rpm for another 20 minutes; the two centrifugates pooled and washed with normal isotonic saline and centrifuged three times to remove the media containing secreted insulin.

The pooled centrifuged cells were first subjected to osmotic lysis by suspending them in 5 ml of sterile distilled water at neutral pH. Next the cells and their membranes were subjected to cryogenic lysis and rupture by alternately freezing the suspension at −80° C with dry ice and acetone and thawing them at 37° C several times. Following the final thawing, the cell-lysate was further sonicated with a Branson ultrasonic sonicator (vibrator) at 3.5 watts for 30 to 60 seconds.

Following the sonication, the entire solution was passed through a sterile Millipore filter (40 Millimicrons). The preparation was further examined under the microscope to ensure that it was free from particles and membrane fragments. This macromolecular preparation was used as the functional genome in the set of transformation experiments. All procedures were done under sterile conditions.

(B) Alternately, using small volumes of cell mass, 5 ml of the entire culture consisting of the fetal beta epithelioid cells and medium alpha were mixed with an equal volume of sterile distilled water; alternately frozen and thawed and sonicated and passed through a Millipore filter (No. 40 m. microns) as described under Method IIA and the entire cell free material was used as the functional genome.

(C) In a second set of studies following treatment of the cells as described under (A) above, the cell free lysate was extracted thrice with equal volumes of Iso-pentylalcohol (Isomylalcohol): Chloroform (1:24), the solvent phases pooled and either freeze dried or air dried at 4° C and reconstituted with sterile water or saline at pH ranging from 7 to 10 (optimal = pH 8) and used as the transforming factor.

(D) In a third set of experiments, the cell lysates were extracted for DNA using Hirt's and other techniques.

In these experiments it was seen that the best results for transformation and eventual insulin production was obtained with functional genome extracted by Method IIA and IIB, although DNA extracts by Methods IIC and IID may also be used.

III. The Methods and Techniques of Transformation of the Fungal Cells with the Human Fetal Insulin Producing Beta Epithelioid Cell The genomic preparations from the specific cells prepared by Methods IIA, IIB, IIC and IID were each incorporated into 5 ml of our Medium alpha whose composition is as follows:

| | |
|---|---|
| Medium 199 with Earle's base GIBCO (Grand Island Biological Company) | 100 ml |
| Liver extract (injectable) (Lilly Lexavite) | 1.0 ml |
| Penicillin | 50,000 units |
| Streptomycin | 50 mg |
| *Nystatin | 5,000 units |

*Alternately Hamycin or Griseofulvin or Amphotericin-B or other anti-fungal agents may be used in this medium and that of Method I.

Five ml of such media in 6 × 1 inch sterile tubes were inoculated with a suspension of the new soil Pseudosaccharomycete TC-1176 and agitated on a Kahn shaker (400 strokes per minute) and incubated at about 27° C (26° to 28° C). After 120 hours, the fungal cells which had been grown in the presence of agents affecting the permeability of the fungal membranes (such as Nystatin, Hamycin, Griseofulvin or Amphotericin B or other anti-fungal agents or membrane permeability agents) and in the presence of the functional genome to enable the fungal cells with altered membrane permeability to incorporate the functional genome within their intracellular structure, were streaked on a Petri plate on glucose yeast agar and incubated for 6 days at about 27° C.

Single spore colonies that developed were selectively isolated, transferred onto slants of the same medium, sub-cultured and conserved for further large scale culture.

To produce insulin from the fungus TC-1176, liquid cultures of both surface and submerged-aerated tyes were prepared. For this purpose, shake flasks and fermentors of different capacities were used. For productivity, submerged cultures have been chiefly used with aeration of 0.25 to 1 volume of sterile air per volume of liquid. Surface-still cultures can also be made with prolonged incubation.

The process for production of insulin using the fungus TC-1176 is similar to the well-known methods employed in the fermentation industry for the production of antibiotics and enzymes. The medium consists of carbohydrate sources such as sugars, alcohols and their esters, starch and oils, and nitrogen sources, both organic and inorganic. The nitrogen sources of organic nature may include various forms of oil cakes, peptones, and protein materials of plant and animal origin, an inorganic nitrogen like nitrates, nitrites, salts of ammonia, urea, etc. and various micro-elements, vitamins and growth promoters. The pH of the medium may range from 2 to 10, depending upon the medium constituents, with an incubation temperature of 16° to 32° C. The broth with the growth of fungus is harvested at the appropriate period of growth which is predetermined by assay procedures and the harvested cells are used for extraction of the active metabolite produced in the fungus cell, which is insulin.

The process of fungal growth is further illustrated by the following examples:

(1) A medium consisting of 3 percent defatted soybean meal, 2 percent glucose, 2 percent glycerine, 0.5 percent yeast extract, 1 percent skim milk powder is mixed in distilled water and the pH adjusted to 6.5 and distributed to 500 ml flasks each with 100 ml medium and sterilized for 30 minutes at 120° C. On cooling, 1 ml of suspension of fungus cells from an 8 day old culture of transformed TC-1176 maintained in the refrigerator, is inoculated and the flasks are placed in a rotary shaker with 220 revolutions per minute in a 28° C constant temperature room. The flasks are checked periodically for steriliity, growth, and utilization of sugars and other constituents. At periods of 40 to 96 hours, when an appropriate growth of cells and biosynthesis of insulin is at its maximum, the flasks are harvested and the mass of yeast cells, with pseudo-mycelial fragments are harvested and the cells washed with several changes of water or saline to free them from the constituents of medium. The filtered or centrifuged cells thus obtained are extracted for insulin.

(2) Medium compositions containing Medium 199 with Earle's base with 1 percent liver extract, penicillin and streptomycin are inoculated and incubated in the same way as in the previous case of Example (1) above and the fungal cells obtained for extracting insulin.

(3) Medium compositions containing sugars mentioned under Example (1) with organic and inorganic nitrogen sources, mineral salts and vitamins are inoculated with TC-1176 cells and incubated at optimum temperature by surface culture process. After an incubation period of 3 to 30 days, depending upon the rate of growth of the fungus strain, the flasks or vessels in which the fungus is grown under sterile conditions are pooled and the fungal cells harvested for further processing and extraction of insulin.

The filtrate which often contains some amount of the active metabolite which is insulin, can also be extracted.

Although the invention is described in terms of specific small scale batch operations, other similar processes in which the large scale growth of the organism TC-1176 referred to for insulin production, by batch fermentation or continuous and semi-continuous fermentation processes and the subsequent harvesting of fungal biomass for the extraction of insulin are part of this invention.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A process for the production of insulin by genetically transformed fungal cells which comprises:
   A. selectively growing insulin producing beta-epithelioid cells from a pancreas and serially sub-culturing the cells under aerated cell growth conditions in a nutrient amino acid-rich medium,
   B. inoculating the rapid growth fungus Pseudosaccharomycete TC-1176 with genomic material extracted from the sub-culture cells and incubating in the presence of an anti-fungal membrane permeability agent to incorporate the functional genome into the fungal cell structure,
   C. incubating the resultant bio-transformed fungal cells in a carbohydrate-nitrogen-rich medium under cell growth conditions, and
   D. separating the fungal cells from the media and extracting the insulin from the cells and supernatant media.

2. A process according to claim 1 further characterized in that said pancreas is human pancreas.

3. A process according to claim 1 for the production of insulin by genetically transformed fungal cells which comprises:
   A. selectively obtaining insulin producing beta epithelioid cells from a pancreas,
   B. dispersing said cells in a nutrient amino acid-rich medium composition in an open aeration incubation vessel maintained at about 32° to 39° C,
   C. initially maintaining said cells under aerated cell growth conditions for several days,
   D. serially sub-culturing the resultant initial culture every several days and reconstituting the original volume with additional medium,
   E. maintaining the sub-cultures under aerated cell growth conditions for a further several days until the desired optimum cell growth level is reached,
   F. separating the cells from the media and extracting genomic material from the cells,
   G. dispersing said genomic material (functional genome) in a further nutrient amino acid-rich medium in an incubation vessel,
   H. inoculating said dispersion with Pseudosaccharomycete TC-1176,
   I. incubating the culture under cell growth conditions in the presence of an anti-fungal membrane permeability agent and mitogen to incorporate the functional genome into the fungal cell structure,
   J. transferring the resultant transformed fungal cells to a carbohydrate-nitrogen-rich medium,
   K. maintaining the culture under cell growth conditions until the desired optimum fungal growth level is reached,
   L. separating the cells from the media and extracting insulin from the cells and from the media.

4. A process according to claim 3 further characterized in that said pancreas is human and said insulin is human insulin.

5. A process according to claim 3 further characterized in that the amino acid-rich medium is Medium 199 with Earle's base supplemented by the addition of minor amounts of liver extract, hydrocortisone and anti-bacterial and anti-fungal antibiotics.

6. A process according to claim 5 further characterized in that said medium composition includes about 5 to 20 ml of liver extract and about 5 to 20 mg of hydrocortisone sulfate per liter of Medium 199.

* * * * *